(12) United States Patent
Malin et al.

(10) Patent No.: US 6,405,065 B1
(45) Date of Patent: Jun. 11, 2002

(54) NON-INVASIVE IN VIVO TISSUE CLASSIFICATION USING NEAR-INFRARED MEASUREMENTS

(75) Inventors: Stephen F. Malin, Glendale, CA (US); Timothy L. Ruchti, Gilbert; Jessica Rennert, Scottsdale, both of AZ (US)

(73) Assignee: Instrumentation Metrics, Inc., Chandler, AZ (US)

( * ) Notice: Subject to any disclaimer, the term of this patent is extended or adjusted under 35 U.S.C. 154(b) by 0 days.

(21) Appl. No.: 09/487,547

(22) Filed: Jan. 19, 2000

Related U.S. Application Data (63) Continuation-in-part of application No. 09/359,191, filed on Jul. 22, 1999, now Pat. No. 6,280,381.
(60) Provisional application No. 60/116,883, filed on Jan. 22, 1999.

(51) Int. Cl.⁷ .................................................. A61B 5/00
(52) U.S. Cl. ........................ 600/310; 600/473; 128/923
(58) Field of Search ................................ 600/310, 314, 600/473, 475; 128/920, 923, 924, 925; 356/402; 250/340, 341.1, 339.01

(56) References Cited

U.S. PATENT DOCUMENTS

| | | | | |
|---|---|---|---|---|
| 5,596,992 A | * | 1/1997 | Haaland et al. | 600/473 |
| 5,945,675 A | | 8/1999 | Malins | 250/339.12 |
| 5,976,885 A | | 11/1999 | Cohenford et al. | 436/63 |

FOREIGN PATENT DOCUMENTS

| WO | WO 99/63057 | 12/1999 |
|---|---|---|

OTHER PUBLICATIONS

*Fisher's Linear Disciminant*. Nonparametric Techniques.
Geladi, P., D. MacDougall, and H. Martens, *Linearization and Scatter–Correction for Near–Infrared Reflectance Spectra of Meat*, Nov. 1985, Applied Spectroscopy.

(List continued on next page.)

*Primary Examiner*—Eric F. Winakur
(74) *Attorney, Agent, or Firm*—Michael A. Glenn; Christopher Peil (57) ABSTRACT

An in vivo, non-invasive method of tissue classification using near-IR (NIR) spectral measurements. A classification model is based on NIR spectral absorbance measurements from an exemplary population. Spectral features representing variation between tissue types are identified. Analytic techniques enhance the features of interest and correct spectral interference to improve the predictive ability of the classification model. A classification routine defines classes based on variation between tissue types, such that variation within a class is small compared to variation between classes. A decision rule assigns individual samples from the exemplary population to classes. An in-vivo, non-invasive procedure applies the classification model to individual tissue samples. A preferred embodiment of the invention distinguishes transgenic mice from non-transgenic individuals based on variation in fat composition within muscle tissue.

47 Claims, 4 Drawing Sheets

OTHER PUBLICATIONS

Johnson, R. and D. Wichern, *Applied Multivariate Statistical Analysis*, 1992, Prentice Hall.

Wanke, R., E. Wolf, W. Hermanns, S. Folger, T. Buchmuller, and G. Brem, *The GH–Transgenic Mouse as an Experimental Model for Growth Research: Clinical and Pathological Studies*, 1992, Veterinary Pathology and Moleculaar Animal Breeding, University of Munich.

Wise, Barry M. and Neal B. Gallagher, *PLS_Toolbox 2.0*, 1998, Eigenvector Research, Inc.

Wolf, E. and R. Wanke, *Growth Hormone Overproduction in Transgenic Mice–Phenotypic Alterations and Deduced Animal Models*.

Susan E. Ebler, Andrew J. Clifford, Takayuki Shibamoto; *Quantitative Analysis by Gas Chromatography of Volatile Carbonyl Compounds in Expired Air From Mice and Human*; 1997;Journal of Chromatography B: Biomedical Applications.

M. Shimoyama et al.; *Nondestructive Discrimination of Biological Materials by Near–Infrared Fourier Transform Raman Spectroscopy and Chemometrics: discrimination Among Hard and Soft Ivories of African Elephants and Mammoth Tusks and Prediction of specific Gravity of the Ivories*: 1997; The Society for Applied Spectroscopy.

\* cited by examiner

NON-INVASIVE IN VIVO TISSUE CLASSIFICATION USING NEAR-INFRARED MEASUREMENTS

This application is a continuation-in-part of S. Malin, T. Ruchti, An Intelligent System for Noninvasive Blood Analyte Prediction, U.S. patent application Ser. No. 09/359,191, filed Jul. 22, 1999, now U.S. Pat. No. 6,280,381 which claims priority from Provisional Patent Application No. 60/116,883, filed Jan. 22, 1999.

BACKGROUND OF THE INVENTION

1. Technical Field

The invention relates to the classification of biological tissue. More particularly the invention relates to a method of classifying tissue using non-invasive, in-vivo near-infrared measurements.

2. Description of the Prior Art

Within the biomedical field, examination of the structure and state of an individual's tissue may yield important information about the individual—for example, the presence or absence of disease, age, or the effect of environmental influences. Tissue biopsy has been an extremely important diagnostic procedure for decades. Additionally, tissue studies are often used to segregate individuals into classes based on the structural and chemical properties of their tissue. For example, transgenic mice have come to play an important role in biomedical research because desired phenotypic and genotypic characteristics can be readily induced by the insertion of foreign genes into their genotype to provide an animal model optimized to the study of a specific scientific problem (see E. Wolfe, R. Wanke, "Growth hormone overproduction in transgenic mice: phenotypic alterations and deduced animal models," *Welfare of Transgenic Animals*, Springer-Verlag, Heidelberg (1996).

It may be difficult to distinguish the transgenic mice from their non-transgenic littermates, and it would be desirable to have a simple, reliable and noninvasive way to do so. The current practice is to sever a portion of each animal's tail in order to obtain enough of the animal's genetic material for use in the various chemical analytical techniques used to study the genome directly ( see R. Wanke, E. Wolf, W. Hermanns, S. Folger, T. Buchmüller, G. Brem, *The GH-Transgenic Mouse as an Experimental Model for Growth Research: Clinical and Pathological Studies* Hormone Research, vol. 37, pp. 74–87 (1992)). Such a procedure injures and traumatizes the animal. In addition, the biopsy procedure can be awkward and require the participation of several people. The chemical analytical techniques are costly and time-consuming, and obtaining the desired information can require several different laboratory procedures and take several days or even weeks. It is also impossible to obtain completely accurate information about the in-vivo structure and state of a tissue when the sample has been subjected to the insult inherent in the biopsy procedure. It would be a technological breakthrough to be able to assess the state and structure of a tissue in-vivo rapidly without relying on tissue biopsy and chemical analytical techniques.

Near infrared (NIR) spectroscopy is a promising noninvasive technology that bases measurements on the absorbance of low energy NIR light that is transmitted into a subject. The light is focused onto a small area of the skin and propagated through subcutaneous tissue. The reflected or transmitted light that escapes and is detected by a spectrometer provides information about the structural and chemical properties of the tissue it has penetrated. The absorbance of light at each wavelength is a function of the structural and chemical properties of the tissue. However, application of NIR spectroscopy to perform accurate, noninvasive tissue typing is presently limited by the inability of current models to compensate for the complexity and dimensionality introduced by dramatic changes in the optical properties that occur in a sample—the skin and living tissue of a subject—as a result of chemical, structural, and physiological variations. Tissue layers, each containing a unique heterogeneous particulate distribution affect light absorbance through scattering and absorbance. Chemical components, such as water, protein, fat, and blood analytes, absorb light proportionally to their concentration through unique absorption profiles, or signatures.

The parent application to the current application, U.S. patent application Ser. No. 09/359,191, An Intelligent System for Noninvasive Blood Analyte Prediction, filed Jul. 22, 1999, by S. Malin, T. Ruchti, discloses a method and apparatus for the use of NIR spectral measurements for predicting blood analyte levels that compensates for co-variation of spectrally interfering species, sample heterogeneity, state variations, and structural variations through an intelligent pattern recognition system. The invention herein disclosed provides a non-invasive method of classifying tissue samples according to chemical and structural properties.

SUMMARY OF THE INVENTION

The invention disclosed herein provides a non-invasive, in vivo method of tissue classification according to chemical and structural properties that employs NIR spectral measurements. A tissue classification model is developed by taking NIR spectral absorbance measurements from an exemplary population of individuals. The spectral measurements are assessed to identify features of interest most likely to represent variation between tissue types. Statistical and analytical techniques are used to enhance the features of interest and extract those features representing variation within a tissue. A classification routine determines the best model to define classes within the exemplary population based on variation between tissue types, such that the variation within a class is small compared to the variation between classes. A decision rule assigns class membership to individual members of the representative population based on the structural and chemical properties of each individual's tissue.

The disclosed tissue classification model is applied in a non-invasive, in-vivo tissue classification procedure using NIR spectral measurements to classify individual tissue samples. The classification model defines classes and provides a set of exemplary data that enable the segregation of test subjects into any of the classes previously defined by the classification model.

A preferred embodiment of the invention is disclosed in which samples of transgenic mice are distinguished from non-transgenic samples based on variation in fat composition of the subcutaneous tissue. The disclosed method correctly classified the samples with an accuracy of 90%.

DETAILED DESCRIPTION

Various features of biological tissue can be measured using NIR spectroscopy because these features often have unique signatures in the NIR wavelength region (700 to 2500 nm) as a result of their absorbance and scattering properties. Many of these features vary according to tissue type and are thus useful for classifying tissue into separate types. Useful features that can be measured using NIR absorbance and scattering patterns include, but are not limited to, thickness of adipose tissue, tissue hydration, magnitude of protein absorbance, scattering properties of the tissue, skin thickness, temperature related effects, age-related effects, spectral characteristics related to sex, path length estimates, volume fraction of blood in tissue, spectral characteristics related to environmental influences, and hematocrit levels. The features that vary according to tissue type may be isolated from tissue sample spectra using statistical techniques and can then be used to classify the sample accordingly.

Development of a Tissue Classification Model

Figure 1:
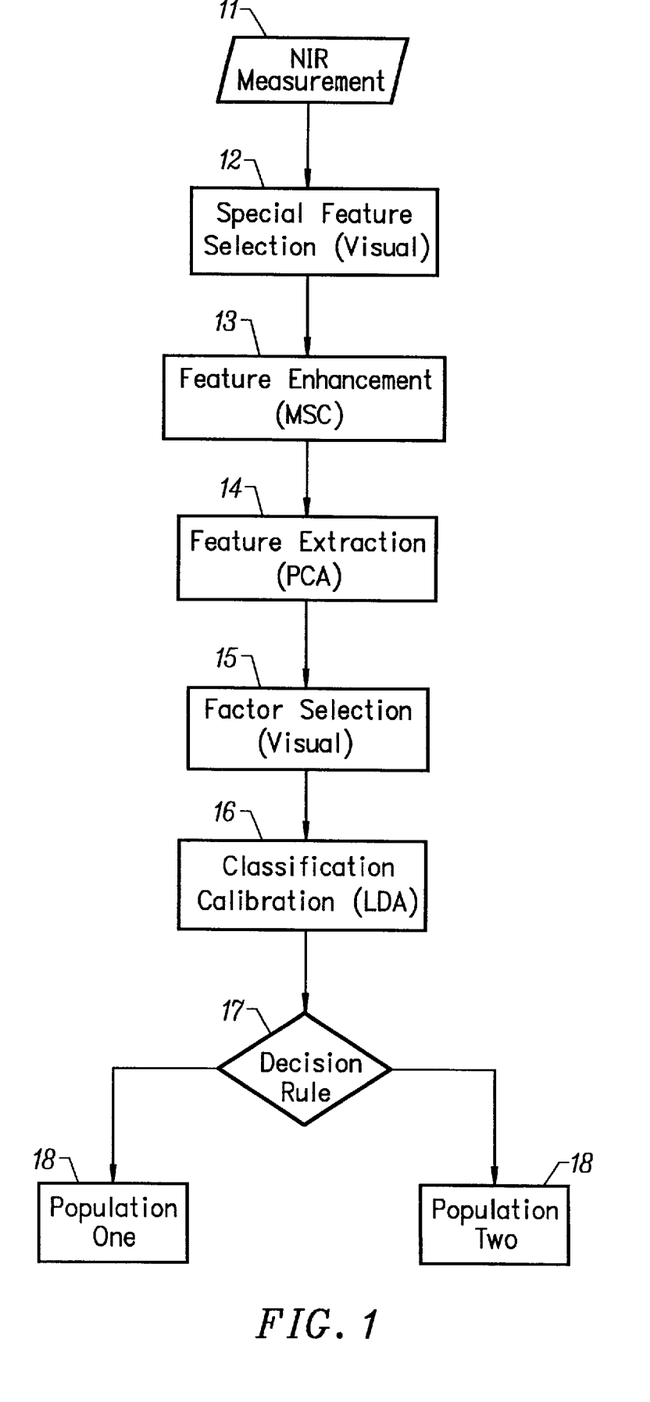
FIG. 1 is a flow diagram showing the steps of a general procedure for tissue sample classification according to the invention.

A non-invasive, in-vivo method for the classification of tissue samples according to chemical, physiological, and structural differences is described herein. The classification model employs the use of NIR measurements to quantify chemical, structural, or physiological properties of the tissue sample. FIG. 1 provides a flow diagram of a general procedure used to develop a classification model. In general, the algorithm for developing a classification model comprises the following steps:

1. Providing exemplary NIR measurements (11)
2. Spectral feature selection (12)
3. Feature enhancement (13)
4. Feature extraction (14)
5. Factor selection (15)
6. Classification calibration (16)
7. Application of a Decision Rule (17)
8. Assignment to a group (18)

Measurement

NIR measurements (11) are first taken from a population of exemplary subjects. The individuals are prepared for the procedure using commonly known methods. In the case of animal subjects, the subjects may need to be anesthetized or immobilized. It is also desirable to prepare the sample surface to be scanned, such that spectral interference due to surface irregularities is minimized. For example, surface hair or fur may need to be removed from animal subjects. A spectrometer detecting light in the near-IR wavelength region (700 to 2500 nm) is employed to collect the NIR measurements. The NIR measurements may be expressed in a variety of units, among them reflectance units and the negative base ten logarithm of reflectance units. While the method of the invention can be employed with various commercially available NIR spectrometers such as the Nicolet Magna-IR 760 or the Perstorp Analytical NIRS 5000, reference is made to FIG. 19 of the parent to this application, U.S. patent application Ser. No. 09/359,191, An Intelligent System for Noninvasive Blood Analyte Prediction, filed Jul. 22, 1999, by S. Malin, T. Ruchti, for a more complete description of an instrument well-suited to the practice of the invention. The sample measurement or tissue absorbance spectrum is the vector $m \in \Re^N$ of absorbance values pertaining to a set of N wavelengths $\lambda \in \Re^N$ that span the near IR wavelength region (700 to 2500 nm).

Feature Selection

Spectral feature selection (12) can comprise a qualitative assessment of the sample spectra to identify the spectral region, or feature of interest in which variation according to tissue type is to be found. The spectra are truncated at the boundaries of the wavelength regions where the tissue-specific variation is present to reduce the complexity and dimensionality of the data set. The data reduction achieved improves the predictive ability of the classification model by reducing the dimensionality of the dataset. Feature selection is aided by comparing the sample spectra with known spectral absorbance patterns, those of protein or fat for example. After one or more wavelength regions containing tissue-specific information have been identified, only these selected regions are used in the classification model.

Feature Enhancement

Once the feature of interest has been identified, a method of feature enhancement (13) is applied to the spectral measurements. Although NIR reflectance measurements are related to chemical and structural features of the tissue samples; the correlation is non-linear, due in large part to the dilution of the spectral measurements by light scatter (see P. Geladi, D. MacDougall, H. Martens, *Linearization and Scatter Correction for Near-infrared Reflectance Spectra of Meat*, Applied Spectroscopy. vol. 39, pp. 491–500 (1985)). Feature enhancement, employing a technique such as multiplicative scatter correction (MSC), corrects interfering spectral variation resulting from changes in the scattering properties of the target tissue volume. In the parent to the present application, U.S. patent application Ser. No. 09/359,191, An Intelligent System for Noninvasive Blood Analyte Prediction, filed Jul. 22, 1999, by S. Malin, T. Ruchti, a method of feature enhancement employing MSC is disclosed. The scatter for each sample is estimated by rotating the sample spectrum and fitting it to a reference spectrum $\bar{m}$ according to $$m = a + b\bar{m} + e \quad (1)$$

where a and b are the slope and intercept and e represents the error in fit. The spectrum is then corrected through $$x = \frac{(m-a)}{b} \quad (2)$$

where x is the processed absorbance spectrum. Thus, each sample's spectrum is standardized such that all samples are normalized with respect to a reference spectrum (see also B. Wise, and N. Gallagher, *PLS Toolbox* 2.0, Eigenvector Research, Inc. Manson (1998). When the feature of interest is due to an absorbing species in the tissue, or if the tissue-specific parameter has distinct spectral shapes, MSC can also be applied to wavelength regions adjacent the feature of interest. Correcting for scatter in adjacent regions causes the characteristic shapes in the uncorrected wavelength regions to be exaggerated. Thus, the targeted chemical and structural features are effectively enhanced.

Feature Extraction

Following feature enhancement, a method of feature extraction is applied to extract those features that are relevant to classification. Feature extraction is accomplished by any mathematical transformation that enhances a quality or aspect of the sample measurement for interpretation. The purpose of feature extraction is to represent concisely the chemical and structural properties and physiological state of the tissue measurement site.

The preferred method of feature extraction, Principal Component Analysis (PCA) (14), is performed on the feature-enhanced data. PCA decomposes the multi-dimensional data into ordered factors that represent the underlying variation within the data set (see R. Johnson and D. Wichern *Applied Multivariate Statistical Analysis*, $3^{rd}$. ed.; Prentice-Hall, New Jersey (1992)). These factors are called principal components. The first principal component represents the most variation present in the data, the second principal component represents the second most variation, the third principal component represents the third most variation and so on. Principal components or factors represent abstract or simple features present in the data. Abstract features represented by the factors do not necessarily have a specific interpretation related to the physical system. Specifically, the scores of a principal component analysis are useful features although their physical interpretation is not always known. However, simple features are derived from an a priori understanding of the sample and can be related directly to a physical phenomenon. Protein and fat, for example, have known absorbance signatures that can be used to determine their contribution to the tissue spectral absorbance. The measured contribution is used as a feature and represents the underlying variable through a single value.

An a priori understanding of the tissue sample aids in the selection of features directly related to physical phenomena of the tissue. The features are represented directly in a vector, $z \in \Re^M$ from the scatter-corrected measurements through $$z = f(\tilde{e}, x) \quad (3)$$

where f. $\Re^n \to \Re^m$ is a mapping from the measurement space to the feature space. Decomposing f(•) yields specific transformations, $f_i(\cdot): \Re^n \to \Re^{m_i}$ for determining a specific feature. The dimension $M_i$, indicates whether the $i^{th}$ feature is a scalar or a vector and the aggregation of all features is the vector z. The features, obtained by reducing the dimensionality of the complex spectral variation, are immediately useful to the tissue classification process. Therefore, feature extraction allows the identification of features representing variation directly attributable to physical phenomena and the exclusion of all others. Thus, a highly dimensional problem is further reduced to a few easily managed dimensions.

Factor Selection

Selection of the factors (15) relevant to the classification model is done by visually inspecting the factor loadings and scores from the factor analysis. As described above, a PCA on the scatter-corrected data set, represented as a data matrix, captures the variation in the data into factors or principal components. For the factors or principal components representing tissue-specific features, the corresponding factor scores separate into groups according to tissue type and the corresponding factor loadings are indicative of the feature responsible for the tissue-specific variation. When the factor scores are represented as scatter plots, the relevant factors or principal components are readily identified through a simple visual inspection.

Classification Calibration

A classification routine (16) with a decision rule (i.e. Fisher's linear discriminant analysis) is applied to the scores of the tissue-specific factor. Classification routines are based on a criterion function that, when maximized, finds the best model to represent the separation between populations (see R. Duda and P. Hart, *Pattern Classification and Scene Analysis*, John Wiley and Sons, New York (1973)). Fisher's linear discriminant analysis (LDA) is the preferred routine used for this classification model. LDA finds the line between the two groups that maximizes the between-class variation and minimizes the within class variation. The LDA criterion function is $$J(w) = \frac{w^t S_b w}{w^t S_w w}, \quad (4)$$

where w is a directional unit vector, $S_b$ is the between-class scatter matrix, and $S_w$ is the within-class scatter matrix. The vector w is selected such that it maximizes the between-class variation/within-class variation ratio. The samples are projected onto w, further reducing the dimensionality of the problem (see R. Duda and P. Hart, *Pattern Classification and Scene Analysis*, John Wiley and Sons, New York (1973)). The criterion function is applied to classify the samples on the basis of the first M scores. In the preferred realization described below, M=3. One skilled in the art can appreciate other methods of classification are readily applicable.

Decision Rule

A decision rule (17) is developed to determine to which class a sample belongs. The criterion the decision rule employs to determine the class membership of the sample is whether the sample's projection (scalar) onto w is greater than or less than the mean of the two population means (see R. Johnson and D. Wichern *Applied Multivariate Statistical Analysis*, $3^{rd}$. ed., Prentice-Hall, New Jersey (1992)). The scalar L is compared with $\overline{L}$, the class boundary. If $L > \overline{L}$, the sample is assigned to population one (18). If not, the sample is assigned to population two (18).

Classification of Tissue Samples

Implementation of the disclosed classification model for classification of actual tissue samples is described in detail in the parent application to the current application, U.S.

patent application Ser. No. 09/359,191, An Intelligent System for Noninvasive Blood Analyte Prediction, filed Jul. 22, 1999 by S. Malin, T. Ruchti. In general, the steps of a procedure for tissue classification are:

1. NIR measurements
2. Feature extraction
3. Pattern classification
4. Assignment of class membership A set of absorbance values pertaining to a set of wavelengths spanning the near infra-red (700 to 2500 nm) is obtained for a new sample. The spectral measurements are pre-processed to attenuate light scatter, noise, and error due to instrument variation without affecting the signal of interest. Feature extraction, previously described, comprises the use of any mathematical transformation that isolates a particular aspect or quality of the sample that is useful for interpretation. Feature extraction is accomplished through the application of one or more multivariate analysis methods, such as principal component analysis, partial least squares, or artificial neural networks. The extracted features are compared to data from a set of predefined classes and the similarity is measured. A decision rule applies a criterion function to assign class membership.

Experiment Results

Introduction

In a preferred embodiment of the invention, the algorithm herein disclosed has been adapted to separate a population of growth hormone transgenic mice from a population of non-transgenic control mice. The embodiment described is specific to transgenic mice. However, the invention is appropriate for the classification of other tissues in other species wherein accurate spectral measurements are possible.

Growth hormone transgenic mice have foreign growth hormone genes inserted into their genome under the control of a promoter gene. The control mice are the non-transgenic littermates of the transgenic mice, and are thus genetically identical to the growth hormone mice except for the presence of the growth hormone gene in the transgenic individuals. The presence of the foreign growth hormone gene causes the subject animal to produce excessive amounts of growth hormone. Compared to non-transgenic mice, transgenic growth hormone mice exhibit a multitude of phenotypic effects secondary to the overproduction of growth hormone, e.g. skeletal gigantism, oversized internal organs, increased body weight, and various characteristic tissue abnormalities (see Wolf et al., see also R. Wanke, E. Wolf, W. Hermanns, S. Folger, T. Buchmüller, G. Brem, *The GH-Transgenic Mouse as an Experimental Model for Growth Research: Clinical and Pathological Studies*, Hormone Research. vol. 37, pp. 74–87 (1992)).

Method

Using diffuse reflectance spectroscopy, NIR measurements were taken from a population of fourteen mice, the population comprising eight growth hormone mice and six controls. Four identical scans were collected from the abdomen of each mouse, once per day for a period of three days. Prior to measurement, the mice were anesthetized using an injectable anesthetic, and shaved using animal trimmers to avoid contamination of the spectral measurements by the subjects' body fur. On each of the three days the animals were selected for scanning in random order from each of their respective populations. A spectrometer setup as previously described was employed for the measurements.

Figure 2:
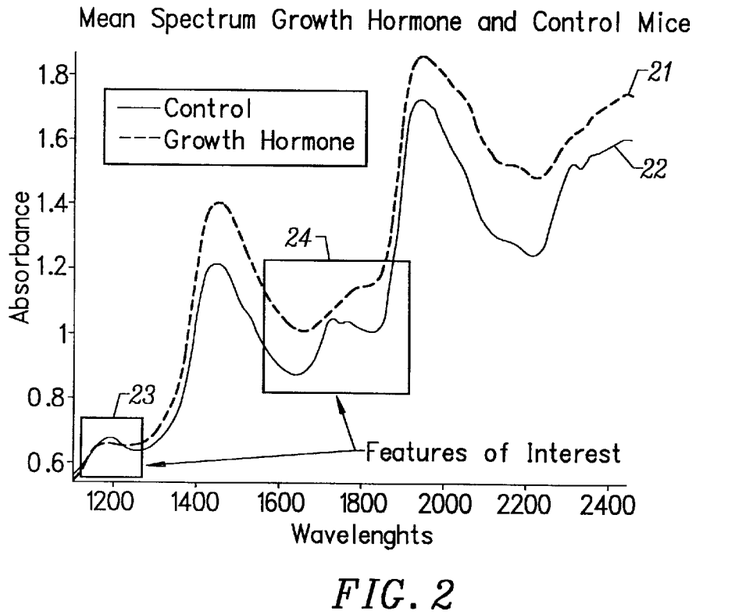
FIG. 2 provides a graph plotting the mean NIR spectra of a population of transgenic growth hormone mice and one of non-transgenic mice, where a first feature of interest in the wavelength region 1100 to 1350 and a second feature of interest in the 1600 to 1880 region are identified, according to the invention.

Using commonly known statistical methods, a mean spectrum for each of the two subject populations was calculated from the original spectral data. FIG. 2 shows the mean spectra of the growth hormone mice (21) and the control mice (22). Visual inspection of the spectra (21 and 22) revealed a divergence in two wavelength regions. A first feature of interest (23) shows that the control mice exhibited an absorbance band in the 1100 to 1350 nm-wavelength region. A second feature of interest (24) revealed an absorbance band in the 1600 to 1880 nm-wavelength region of the spectrum from the control mice. Unlike the controls, the transgenic subjects did not exhibit such absorbance bands.

Figure 3:
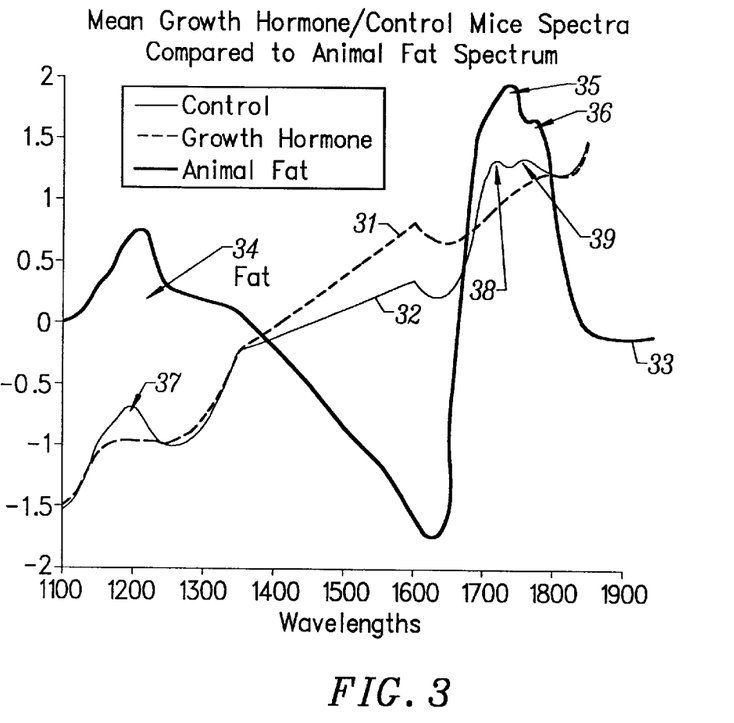
FIG. 3 provides a graph comparing the absorbance bands at the features of interest within the mean NIR spectra of FIG. 2 with the absorbance bands of a sample of animal fat according to the invention.

FIG. 3 shows a comparison of the mean spectra of the two mouse populations (31 and 32) with the spectrum of a sample of pure animal fat (33), within the two identified wavelength regions (features of interest). The animal fat spectrum clearly shows a first absorbance band (34) in the 110 to 1350 nm-wavelength region and second (35) and third (36) absorbance bands in the 1600 to 1880 nm-wavelength region. A first absorbance band (37) and second and third absorbance bands (38, 39) in the mean spectrum of the control population mirrors the absorbance bands (34, 35, 36) of the fat spectrum. At the same time, analogous absorbance bands are absent from the mean spectrum of the transgenic GH population, suggesting that the difference in the spectra of the two mouse populations was due to a difference in the fat composition of the tissues.

Figure 4:
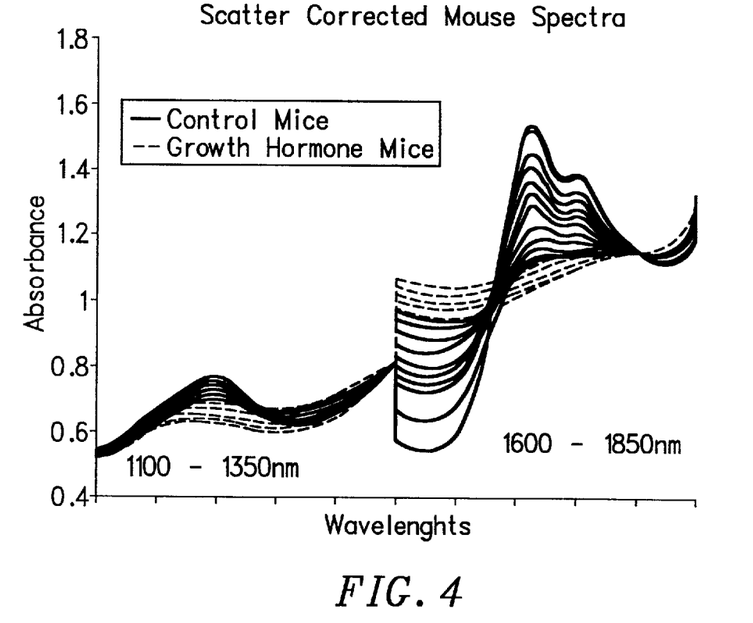
FIG. 4 provides a graph showing the features of interest of FIG. 2 enhanced by scatter correction according to the invention.

Multiplicative Scatter Correction (MSC), as described earlier was applied to enhance the features of interest. FIG. 4 provides a graph of the scatter-corrected spectral data. It is clear from the scatter-corrected spectra that the observed absorbance bands are expressed to varying degrees within the population of samples. A large number of the samples exhibit no noticeable absorbance bands, while other exhibit pronounced absorbance bands.

Figure 5:
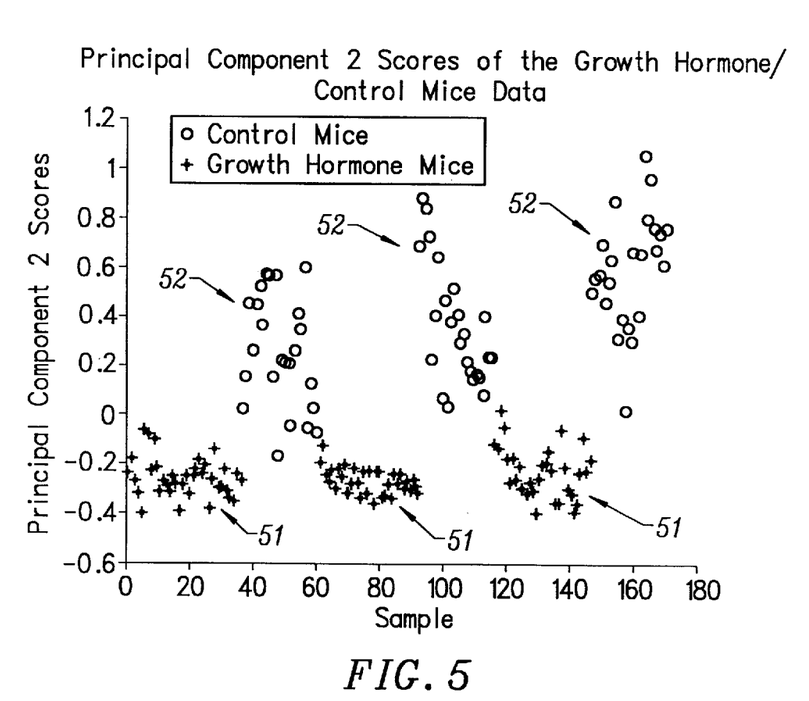
FIG. 5 provides a scatter plot showing factor scores of a second principal component from Principal Component Analysis of the second feature of interest of FIG. 2 according to the invention.
Figure 6:
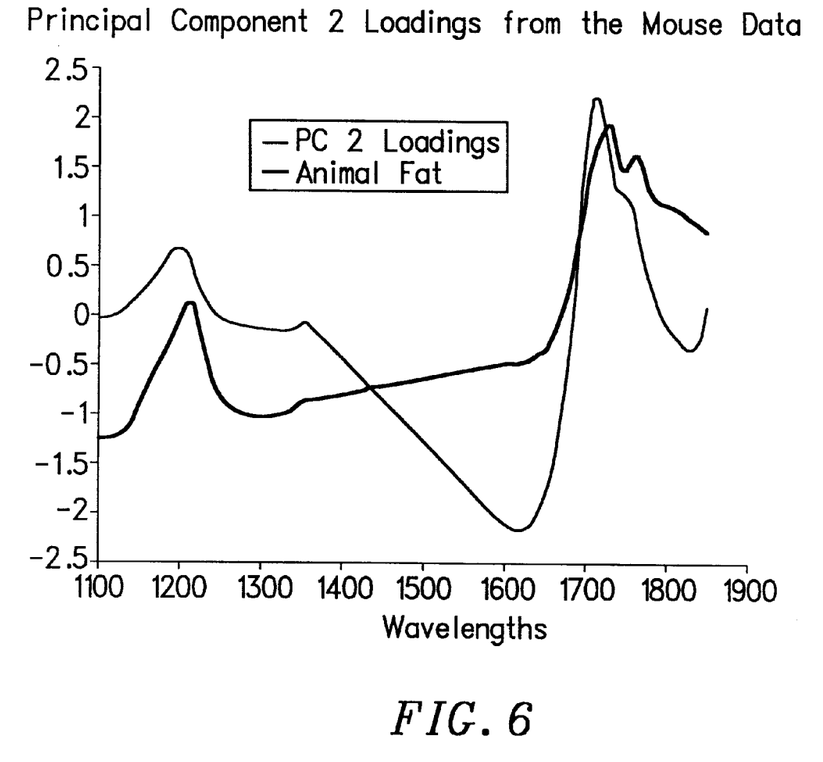
FIG. 6 provides a graph of factor loadings of the second principal component of FIG. 5 with the animal fat spectrum of FIG. 3 according to the invention.

Principal Component Analysis was performed on the scatter-corrected data from the wavelength regions of 1100 to 1350 nm and 1600 to 1850 nm. Visual inspection of the resulting factor scores revealed the second principal component to be significant. As FIG. 5 shows, the factor scores for the second principal component separate neatly into two groups (51, 52) corresponding to the two mouse populations. The graph of FIG. 6 shows a clear correlation between the absorbance bands of the animal fat spectrum and the principal component 2 loadings, further evidence that the separation between the two mouse populations is due to the fat composition of the tissues.

Fisher's linear discriminant analysis was applied to the first three principal components scores to define an appropriate model for the classes such that within class variation was minimized and between-class variation is maximized.

"Leave-one-out" cross-validation, a calibration routine particularly well suited for application with small data sets, was used in the validation of the classification calibration. For this analysis, an iterative process was employed in which one sample was left out of the data set, the remaining samples were used to develop a calibration, and the resulting calibration was used to predict the sample left out. The process is repeated until all the samples have been left out and predicted.

Results

The results of the calibration routine are presented in Table 1 below.

TABLE 1

Cross Validation Classification Results

| Type | Misclassified | Correct | Total | % Correct |
|---|---|---|---|---|
| Growth Hormone | 0 | 99 | 99 | 100% |
| Control | 17 | 52 | 72 | 72% |
| Total | 17 | 154 | 171 | 90% |

A total of 171 spectral samples were examined, 99 spectral samples from GH transgenic individuals, and 72 samples from the controls. Of the samples, 99 or 100% of the transgenic samples were correctly classified; 54 or 72% of the control samples were correctly classified. Thus the algorithm correctly classified each of this population of samples with an accuracy of 90%. The two mouse populations were classified according to the chemical and structural differences in their tissue, without resorting to invasive biopsy procedures. Data collection was readily performed by one person and an online classification could be developed that would require a few minutes as opposed to the days or weeks that may be required with conventional methods.

Discussion

Although the current embodiment is directed to the classification of mice based on structural and chemical differences in their tissues, those skilled in the art will readily appreciate that the use of NIR measurements to indicate chemical, structural, and physiological variation in tissue has application in other fields of endeavor, for example non-invasive blood analyte prediction, wound healing research and dermatological disease therapy.

The class definitions described here have been defined for a specific population of subjects, and cannot be generalized to all subjects. A classification model suitable for all subjects includes a sufficient number of samples to model the total range of variation in the population for a specific tissue parameter. While the present embodiment employs a specific number of features, classes, decision rules, and classification models, the invention may use an arbitrary number of each in the configuration shown to classify tissue samples. While the experimental results demonstrate the validity and benefit of the invention, accuracy of the results is directly dependent on the accuracy of the spectral measurements. Further improvement to results accuracy is achieved through improvements in the noise level and the resolution of the spectrometer.

Although the invention is described herein with reference to certain embodiments, one skilled in the art will readily appreciate that other applications may be substituted for those set forth herein without departing from the spirit and scope of the present invention. Accordingly, the invention should only be limited by the Claims included below.

What is claimed is:

1. A method of developing a classification model for classification of tissue samples comprising the steps of:
   providing a set of measured absorbance spectra from a population of exemplary subjects;
   visually inspecting said spectra;
   comparing said spectra with known spectral absorbance patterns;
   selecting at least one feature of interest wherein variation according to issue type may be found based on observed similarities between said sample spectra and said known spectral absorbance patterns
   enhancing said one or more features of interest by correcting said spectra for light scatter;
   extracting at least one feature of interest relevant to classification;
   selecting factors of said features of interest related to structural and chemical properties of said samples;
   defining classes for said tissue samples on the basis of structural and state similarity, wherein variation within a class is small compared to variation between classes; and
   assigning class membership.

2. The method of claim 1, wherein each of said measured absorbance spectra are represented as a vector $m \in \Re^N$ of absorbance values pertaining to a set of N wavelengths $\lambda \in \Re^N$ spanning the wavelength region of 700 to 2500 nm.

3. The method of claim 1, wherein said step of selecting at least one feature of interest further comprises:
   truncating said spectra at the boundaries of said at least one selected feature of interest.

4. The method of claim 1, wherein said step of correcting said spectra comprises:
   employing multiplicative scatter correction.

5. The method of claim 4, wherein scatter for each of said sample spectra is estimating by rotating said sample spectra to a reference spectrum $\bar{m}$ according to:

$$m = a + b\bar{m} + e$$

where a and b are the slope and intercept and e is the error in fit; and wherein each of said spectra are corrected through:

$$x = \frac{(m-a)}{b}$$

where x is the corrected absorbance spectrum.

6. The method of claim 1, wherein said feature extraction step further comprises the steps of:
   applying a mathematical transformation wherein said feature-enhanced sample spectra are decomposed to distinct factors that represent underlying variation within the data set;
   employing factor-based methods to determine which of said factors are attributable to a known spectral absorbance pattern; and
   including the measured contribution of said known spectral absorbance pattern to the sample spectral absorbance as features.

7. The method of claim 6, wherein said extracted features are represented from said scatter-corrected measurements, x, in a vector $z \in \Re^M$ through:

$$z = f(\bar{e}, x)$$

$f: \Re^n \to \Re^m$ being a mapping from a measurement space to a feature space; wherein decomposing $f(\bullet)$ yields specific transformations $f_i(\bullet): \Re^n \to \Re^{m_i}$ whereby specific factors are determined; wherein the dimension $M_i$ indicates whether the $i^{th}$ factor is any of a scalar and a vector; and wherein the aggregation of all of said factors is the vector z, and wherein $\bar{e}$ represents wavelength.

8. The method of claim 7 further comprising the steps of: including factors represented as vectors in the data set; and excluding those factors represented as scalars from the data set.

9. The method of claim 1, wherein said factor selection step further comprises the steps of:
representing variation within said measured spectra as factor loadings; and
representing the weight of a particular sample on said spectral variation as factor scores corresponding to said factor loadings.

10. The method of claim 9, wherein a clustering of said factor scores represents a variation according to tissue type and said factor loadings represent a feature responsible for tissue-specific variation.

11. The method of claim 1, wherein said set of defining classes comprises:
employing means for defining classes, wherein within-class variation is minimized and between-class variation is maximized.

12. The method of claim 11 wherein said means for defining classes comprises linear discriminant analysis.

13. The method of claim 12, wherein said discriminant analysis employs a criterion function:

$$J(w) = \frac{w^t S_b w}{w^t S_w w},$$

where w is a directional unit vector, $S_b$ is the between class scatter matrix, $S_w$ is the within-class scatter matrix, wherein a vector w is selected such that the between-class variation/within-class variation ratio is maximized, wherein said vector w represents the separation between classes.

14. The method of claim 13, further comprising the step of:
applying said criterion function on the basis of the first M scores, where M is an arbitrary number, wherein each of said samples are projected onto said vector w; wherein said projections onto said vector w are scalars.

15. The method of claim 14, wherein said decision rule represents said scalars of said samples as L, and $\overline{L}$ represents a boundary between said classes; and
wherein assignment to a first class is based on the condition $L > \overline{L}$; and
wherein assignment to a second class is based on the condition $L < \overline{L}$.

16. The method for classifying tissue comprising the steps of:
providing a new set of spectral absorbance measurements from a test subject;
extracting features corresponding to tissue-specific variation;
employing a classification model to compare said extracted features with a set of exemplary measurements; and
assigning class membership through application of a decision rule, wherein said features are represented in a vector $z \in \Re^M$ that is determined through:

$$z = f(\lambda, x)$$

where $f: \Re^N \to \Re^M$ is a mapping from a measurement space to a feature space, wherein decomposing $f(\bullet)$ yields specific transformations, $f_i: \Re^N \to \Re^{M_i}$ for determining a specific feature, wherein the dimension $M_i$ indicates whether an $i^{th}$ feature is a scalar or vector and an aggregation of all features is the vector z, and wherein a feature exhibits a certain structure indicative of an underlying physical phenomenon when said feature is represented as a vector or a pattern.

17. The method of claims 16, wherein said feature extraction step comprises any mathematical transformation that enhances a quality or aspect of sample measurement for interpretation to represent concisely structural properties and physiological state of a tissue measurement site, wherein a resulting set of features is used to classify a subject.

18. The method of claim 16, wherein said classification model comprises means for determining a set of similarity measures with predefined classes.

19. The method of claim 18, further comprising the step of:
providing a classification system that assumes that said classes are mutually exclusive and that forces each measurement to be assigned to a single class.

20. The method of claim 16 wherein said decision rule comprises means for assigning class membership on the basis of a set of measures calculated by a decision engine.

21. The method of claim 16, wherein said pattern classification step further comprises the steps of:
measuring the similarity of a feature to predefined classes; and
assigning class membership.

22. The method of claim 21, wherein said measuring step uses mutually exclusive classes and assigns each measurement to one class.

23. The method of claim 22, further comprising the step of:
using measurements and class assignments to determine a mapping from features to class assignments.

24. A method of developing a classification model for distinguishing transgenic mice from non-transgenic mice based on fat composition in the tissue comprising the steps of:
providing a set of spectral absorbance measurements from an exemplary population of subject animals;
selecting one or more features of interest within said spectral measurements wherein variation according to tissue type may be found;
enhancing said one or more features of interest;
extracting at least one feature of interest relevant to classification;
selecting factors of said features of interest related to structural and chemical properties of said samples;
defining classes for said tissue samples on the basis of structural and state similarity, wherein variation within a class is small compared to variation between classes; and
assigning class membership.

25. The method of claim 24, wherein said transgenic mice are foreign growth hormone transgenic mice.

26. The method of claim 24, wherein each of said measured absorbance spectra are represented as a vector $m \in \Re^N$ of absorbance values pertaining to a set of N wavelengths $\lambda \in \Re^N$ spanning the wavelength region of 700 to 2500 nm.

27. The method of claim 24, wherein said feature extraction step further comprises the steps of:

visually inspecting said absorbance spectra;

comparing said absorbance spectra with the spectral absorbance pattern of animal fat;

selecting said one or more features of interest based on observed similarities between said sample spectra and said spectral absorbance pattern of animal fat; and truncating said sample spectra at the boundaries of said one or more selected features of interest.

28. The method of claim 27, wherein said feature extraction step further comprises the steps of:

applying a mathematical transformation wherein said feature-enhanced sample spectra are decomposed to distinct factors that represent underlying variation within the data set;

employing factor-based methods to determine which of said factors are attributable to said animal fat spectral absorbance pattern; and including the measured contribution of said animal fat spectral absorbance pattern to the sample spectral absorbance as features.

29. The method of claim 28, wherein said extracted features are represented from said scatter-corrected measurements, x, in a vector $z \in \Re^M$ through:

$$z = f(\ddot{e}, x)$$

$f: \Re^n \to \Re^m$ being a mapping from a measurement space to a feature space; wherein decomposing $f(\bullet)$ yields specific transformations $f_i(\bullet): \Re^n \to \Re^{m_i}$ whereby specific factors are determined; wherein the dimension $M_i$ indicates whether the $i^{th}$ factor is any of a scalar and a vector; and wherein the aggregation of all of said factors is the vector z, and wherein $\ddot{e}$ represents wavelength.

30. The method of claim 28, wherein loading of said factors represent variation according to fat composition of tissue, and scores of said factors identify different subject classes based on fat composition in the tissue.

31. The method of claim 24, wherein said feature enhancement step comprises:

employing means for correcting said sample spectra for light scatter.

32. The method of claim 31 wherein said means for correcting said spectra comprises multiplicative scatter correction.

33. The method of claim 32, wherein scatter for each of said sample spectra is estimating by rotating said sample spectra to a reference spectrum $\bar{m}$ according to:

$$m = a + b\bar{m} + e$$

where a and b are the slope and intercept and e is the error in fit; and wherein each of said spectra are corrected through:

$$x = \frac{(m-a)}{b}$$

where x is the corrected absorbance spectrum.

34. The method of claim 24, wherein said class definition step defines classes for said population based on variation according to fat composition in the tissue, such that within-class variation is minimized and between-class variation is maximized.

35. The method of claim 24, wherein said class assignment step employs a decision rule to assign membership to individuals from said sample population.

36. A method of distinguishing transgenic mice from non-transgenic mice based on variation according to fat composition in the tissue comprising the steps of:

providing a new set of spectral absorbance measurements from a subject;

extracting features corresponding to tissue-specific variation;

performing pattern classification, wherein a classification model compares said extracted features with a set of exemplary measurements; and assigning class membership through application of a decision rule.

37. The method of claim 36, wherein said transgenic mice are foreign growth hormone transgenic mice.

38. The method of claim 36, wherein said feature extraction step comprises any mathematical transformation that enhances a quality or aspect of sample measurement for interpretation to represent concisely structural properties and physiological state of a tissue measurement site, wherein a resulting set of features is used to classify said subject according to fat composition in the tissue.

39. The method of claim 36, wherein said classification model comprises means for determining a set of similarity measures with predefined classes.

40. The method of claim 39, wherein said classes are defined on the basis of fat composition in the tissue.

41. The method of claim 39, further comprising the step of:

providing a classification system that assumes that said classes are mutually exclusive and that forces each measurement to be assigned to a single class.

42. The method of claim 41 wherein said features are represented in a vector $z \in \Re^M$ that is determined through:

$$z = f(\lambda, x)$$

where $f: \Re^N \to \Re^M$ is a mapping from a measurement space to a feature space, wherein decomposing $f(\bullet)$ yields specific transformations, $f: \Re^N \to \Re^{M_i}$ for determining a specific feature, wherein the dimension $M_i$ indicates whether an $i^{th}$ feature is a scalar or vector and an aggregation of all features is the vector z, and wherein a feature exhibits a certain structure indicative of variation according to fat composition in the tissue when said feature is represented as a vector or a pattern.

43. The method of claim 36, wherein said decision rule comprises means for assigning class membership on the basis of a set of measures calculated by a decision engine.

44. The method of claim 36, wherein said pattern classification step further comprises the steps of:

measuring the similarity of a feature to predefined classes; and assigning class membership.

45. The method of claim 44, wherein said predefined classes are any of transgenic mice and non-transgenic mice.

46. The method of claim 45, wherein said classes are mutually exclusive.

47. The method of claim 46, further comprising the step of:

using measurements and class assignments to determine a mapping from features to class assignments.

* * * * *